(12) United States Patent
Abdelgany (10) Patent No.: US 7,367,979 B2
(45) Date of Patent: May 6, 2008

(54) SCREWDRIVER

(75) Inventor: Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 287 days.

(21) Appl. No.: 11/063,452

(22) Filed: Feb. 23, 2005

(65) Prior Publication Data

US 2005/0188469 A1    Sep. 1, 2005

Related U.S. Application Data

(60) Provisional application No. 60/548,543, filed on Feb. 27, 2004.

(51) Int. Cl.
*A61B 17/58* (2006.01)
*A61B 17/60* (2006.01)

(52) U.S. Cl. .................. 606/104; 606/205; 606/99; 81/436

(58) Field of Classification Search ............... 606/104, 606/105, 205, 208, 99, 86, 207; 81/111, 81/93, 109, 436
See application file for complete search history.

(56) References Cited

U.S. PATENT DOCUMENTS

| | | | |
|---|---|---|---|
| 2,426,197 A * | 8/1947 | Greer | 81/453 |
| 2,513,956 A * | 7/1950 | Ollagnon | 81/93 |
| 4,997,432 A | 3/1991 | Keller | |
| 5,139,499 A | 8/1992 | Small et al. | |
| 5,391,181 A | 2/1995 | Johnson et al. | |
| 5,423,819 A | 6/1995 | Small et al. | |
| 5,423,855 A * | 6/1995 | Marienne | 606/208 |
| 5,484,440 A | 1/1996 | Allard | |
| 5,591,176 A * | 1/1997 | Henderson et al. | 606/137 |
| 5,653,729 A * | 8/1997 | Chappuis et al. | 606/207 |
| 5,946,988 A | 9/1999 | Metz-Stavenhagen | |
| 6,139,549 A | 10/2000 | Keller | |
| 6,602,260 B2 | 8/2003 | Harari et al. | |
| 6,976,988 B2 * | 12/2005 | Ralph et al. | 606/99 |
| 7,204,852 B2 * | 4/2007 | Marnay et al. | 623/17.16 |

* cited by examiner

*Primary Examiner*—Pedro Philogene
(74) *Attorney, Agent, or Firm*—Mohammad S. Rahman, Esq.; Gibb & Rahman, LLC (57) ABSTRACT

A scissor-action screwdriver and screwdriver attachment comprises a plurality of arms pivotally attached to one another; a bias element mounted in at least one of the plurality of arms; and a sleeve slidably mounted around at least one of the plurality of arms, wherein the plurality of arms comprise a first arm and a second arm, and wherein each of the plurality of arms preferably comprise a prong end. The screwdriver attachment further comprises a stop component adapted to limit a distance of separation between the first arm and the second arm. Additionally, the bias element may comprise a spring. Moreover, each of the plurality of arms preferably comprises a tapered section, wherein the sleeve comprises an inner tapered wall adapted to engage the tapered section of each of the plurality of arms. The screwdriver further includes a handle connected to the second arm.

20 Claims, 11 Drawing Sheets

SCREWDRIVER

CROSS REFERENCE TO RELATED APPLICATION

This application claims the benefit of U.S. Provisional Patent Application No. 60/548,543 filed on Feb. 27, 2004, the contents of which in its entirety is herein incorporated by reference.

BACKGROUND OF THE INVENTION

1. Field of the Invention

The embodiments of the invention generally relate to tools, and more particularly to a tool used to drive a bone screw implant assembly used in the field of surgical lumbar, thoracic and cervical spine treatment.

2. Description of the Related Art

Surgical procedures treating spinal injuries are one of the most complex and challenging surgeries for both the patient and the surgeon. When there are various deformities, trauma, or fractures of the vertebra, surgeons may attempt to "fuse" them together by attaching screw-like assemblies into the pedicles of the spine and thereby connecting several vertebrae (typically two or more) using a semi-rigid rod. These screw-like assemblies may include the type of assemblies described in U.S. patent application Ser. No. 11/045,908, filed Jan. 28, 2005 and entitled, "Polyaxial Pedicle Screw Assembly," the complete disclosure of which in its entirety is herein incorporated by reference. Generally, assemblies such as these include a bone screw and a screw head attached to the bone screw.

Those in the industry, as well as orthopedic surgeons, have acknowledged that having a bone screw pre-attached to the screw head prior to the time of the surgical operation, and preferably being attached by the manufacturer, is advantageous as it reduces the overall time associated with performing the operation. However, once a pre-attached pedicle screw assembly (combined bone screw and screw head) is received by the surgeon, he/she still has to screw (drive) the bone screw into the bone. Unfortunately, most conventional tools cannot drive the bone screw into the bone with the screw head attached due to the spatial limitations inside of the patient and the overall complex geometry resulting from the pedicle screw assembly (combined bone screw and screw head). Thus, there remains a need for a new tool to drive these pedicle screw assemblies (combined bone screw and screw head) into the bone, thereby reducing the overall surgical time and providing the surgeon with improved intra-operative flexibility.

SUMMARY OF THE INVENTION

In view of the foregoing, an embodiment of the invention provides a screwdriver attachment comprising a plurality of arms pivotally attached to one another; a bias element mounted in at least one of the plurality of arms; and a sleeve slidably mounted around at least one of the plurality of arms, wherein the plurality of arms comprise a first arm and a second arm, and wherein each of the plurality of arms preferably comprise a prong end. The screwdriver attachment further comprises a stop component adapted to limit a distance of separation between the first arm and the second arm. Additionally, the bias element may comprise a spring. Moreover, each of the plurality of arms preferably comprises a tapered section, wherein the sleeve comprises an inner tapered wall adapted to engage the tapered section of each of the plurality of arms.

Another aspect of the invention provides a scissor-action tool comprising a first arm; a second arm pivotally attached to the first arm; a bias element adjacent to the first and second arms; and a sleeve mounted over the second arm, wherein each of the first and second arms preferably comprising a prong end. The tool further comprises a stop component adapted to limit a distance of separation between the first and second arms. Furthermore, the bias element may comprise a spring. Also, each of the first and second arms preferably comprises a tapered section, wherein the sleeve is slidably mountable over the first arm and comprises an inner tapered wall adapted to engage the tapered section of each of the first and second arms.

Another embodiment of the invention provides a screwdriver comprising a handle; a first arm; a second arm connected to the handle and the first arm; a spring in contact with the first and second arms; and a sleeve mounted around the second arm. The screwdriver further comprises a stop component adapted to limit a distance of separation between the first and second arms. Preferably, each of the first and second arms comprises a tapered section, wherein the sleeve is preferably slidably mountable around the first arm and comprises an inner tapered wall adapted to engage the tapered section of each of the first and second arms. Preferably, each of the first and second arms comprises a prong end, wherein the prong end may be adapted to engage a fixation component of a pedicle screw assembly. Additionally, the first arm may be pivotally connected to the second arm.

These and other aspects of the embodiments of the invention will be better appreciated and understood when considered in conjunction with the following description and the accompanying drawings. It should be understood, however, that the following descriptions, while indicating preferred embodiments of the invention and numerous specific details thereof, are given by way of illustration and not of limitation. Many changes and modifications may be made within the scope of the embodiments of the invention without departing from the spirit thereof, and the embodiments of the invention include all such modifications.

BRIEF DESCRIPTION OF THE DRAWINGS

The embodiments of the invention will be better understood from the following detailed description with reference to the drawings, in which.

DETAILED DESCRIPTION OF PREFERRED EMBODIMENTS OF THE INVENTION

The embodiments of the invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments of the invention. The examples used herein are intended merely to facilitate an understanding of ways in which the embodiments of the invention may be practiced and to further enable those of skill in the art to practice the embodiments of the invention. Accordingly, the examples should not be construed as limiting the scope of the embodiments of the invention.

As mentioned, there remains a need for a new tool to drive pedicle screw assemblies (combined bone screw and screw head) into the bone, thereby reducing the overall surgical time and providing the surgeon with improved intra-operative flexibility. The embodiments of the invention address this need by providing a scissor-action screwdriver capable of performing this function without having to remove and attach excess parts and accessories. Referring now to the drawings and more particularly to FIGS. 1 through 17 where similar reference characters denote corresponding features consistently throughout the figures, there are shown preferred embodiments of the invention.

Figure 1A:
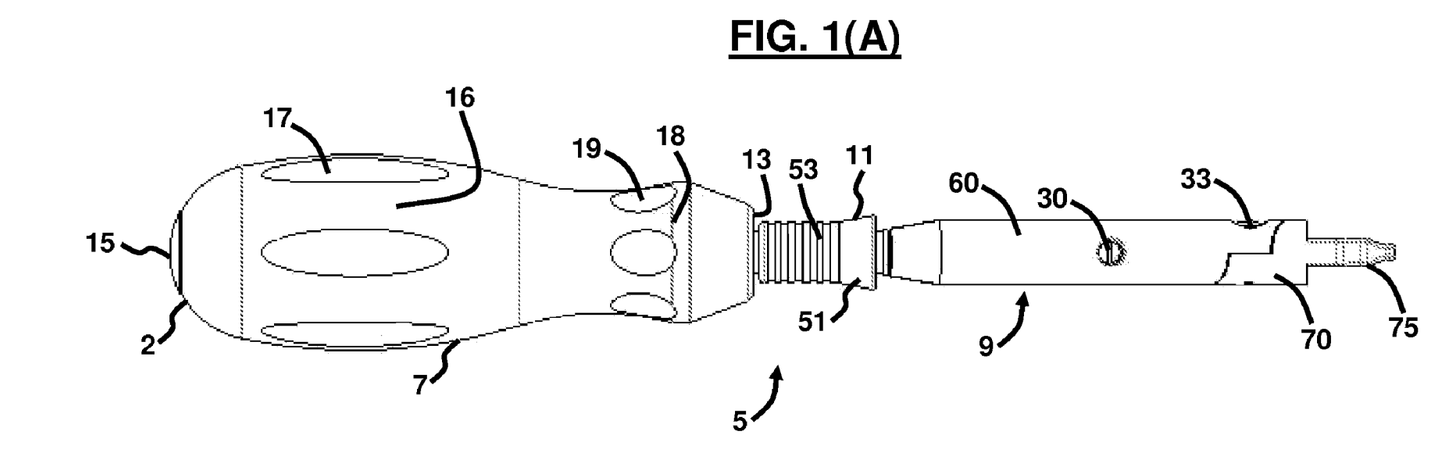
FIG. 1(A) illustrates a top view of a screwdriver according to a first embodiment of the invention.
Figure 1B:
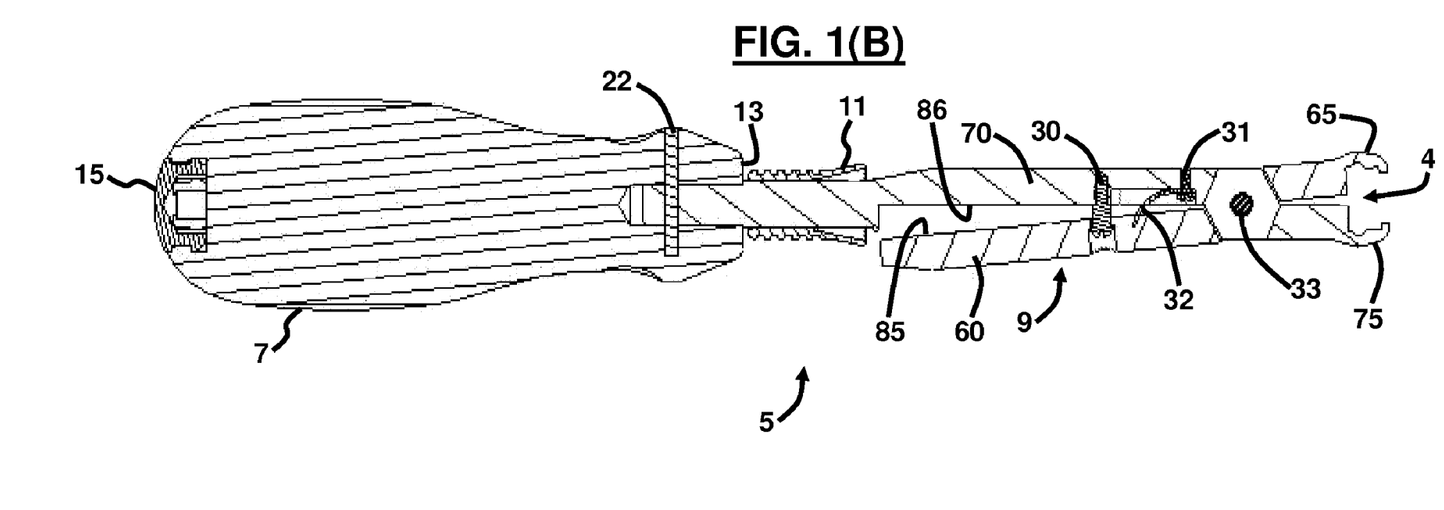
FIG. 1(B) illustrates a cross-sectional side view of the screwdriver of FIG. 1(A) according to a first embodiment of the invention.
Figure 2A:
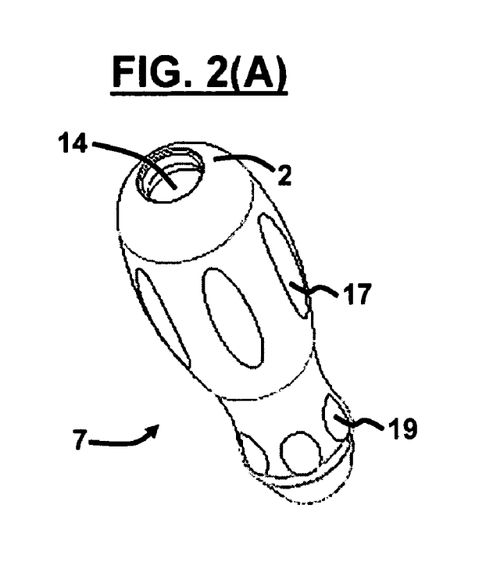
FIG. 2(A) illustrates a perspective view of the handle of FIG. 1(A) according to a first embodiment of the invention.
Figure 2B:
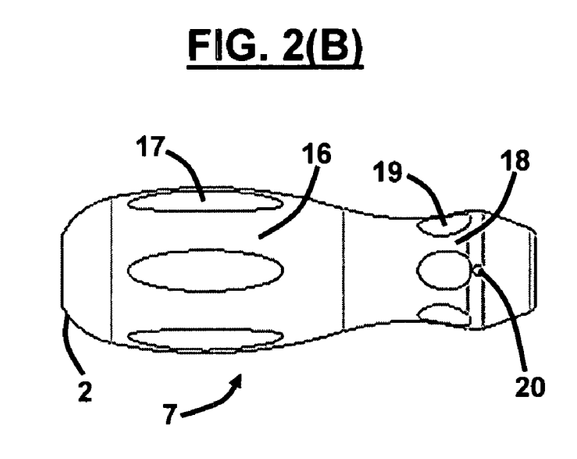
FIG. 2(B) illustrates a front view of the handle of FIG. 2(A) according to a first embodiment of the invention.
Figure 2C:
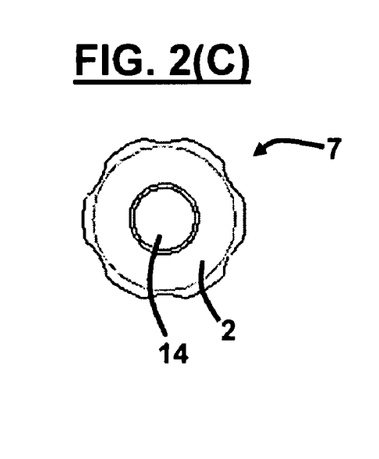
FIG. 2(C) illustrates a side view of the handle of FIG. 2(A) according to a first embodiment of the invention.
Figure 2D:
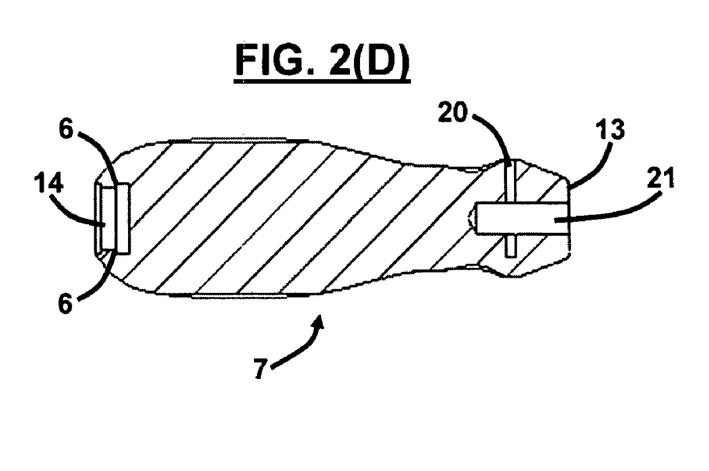
FIG. 2(D) illustrates a cross-sectional view of the handle of FIG. 2(B) according to a first embodiment of the invention.

A first embodiment of the screwdriver 5 is illustrated in FIGS. 1(A) and 1(B). The screwdriver 5 generally includes a handle 7, an attachment mechanism 9, and a sleeve 11 adapted to fit around the attachment mechanism 9. The attachment mechanism 9 is adapted to attach to the handle 7, but can be removed if necessary. The handle 7 is further shown in FIGS. 2(A) through 2(D) (with reference to FIGS.

1(A) and 1(B)). The handle 7 comprises an enlarged bulbous end 16 comprising a plurality of generally elongated gripping features 17 configured circumferentially around the bulbous end 16. The bulbous end 16 terminates with a tip portion 2. Additionally, the handle 7 includes a generally slimmer attachment end 18 comprising a plurality of generally elongated gripping features 19 similarly configured circumferentially around the attachment end 18. The gripping features 17, 19 aid in facilitating a better grip during torsional maneuvering of the screwdriver 5 of FIGS. 1(A) and 1(B).

Again, with reference to FIGS. 2(A) through 2(D), the attachment end 18 further includes a hole 20 configured transverse to the elongated plane of the handle 7 and further preferably configured approximately three-quarters of the width of the attachment end 18. Additionally, an attachment bore 21 is configured in the bottom end 13 of the handle 7 and configured transverse to the hole 20. The handle 7 further includes a top hole 14 configured in the bulbous end 16 of the handle 7 and opposite to the attachment bore 21. The top hole 14 further includes a generally circular lip 6 configured circumferentially around the top hole 14. The handle 7 illustrated in FIGS. 1(A) through 2(D) is merely an example of the type of handle which may be used in conjunction with the embodiments of the invention. Those skilled in the art would readily appreciate that various other handle configurations could be used in conjunction with the embodiments of the invention, and the embodiments of the invention are not restricted to any one type of configuration.

Figure 3A:
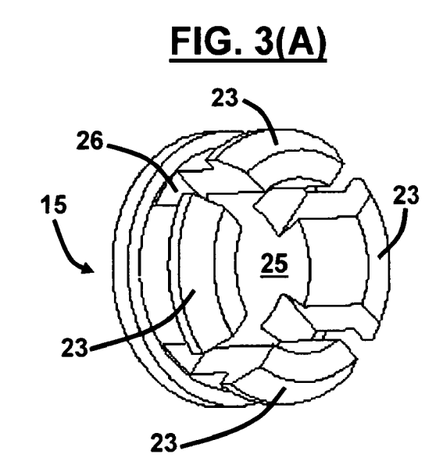
FIG. 3(A) illustrates a perspective view of the handle top of FIG. 1(A) according to a first embodiment of the invention.
Figure 3B:
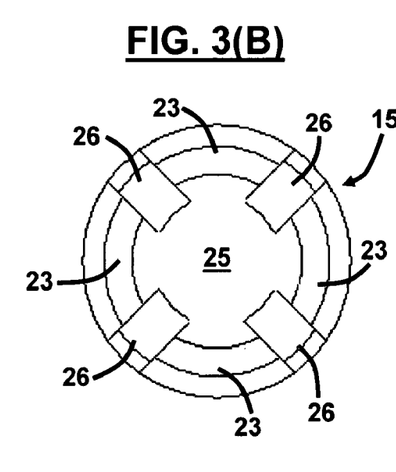
FIG. 3(B) illustrates a top view of the handle top of FIG. 3(A) according to a first embodiment of the invention.
Figure 3C:
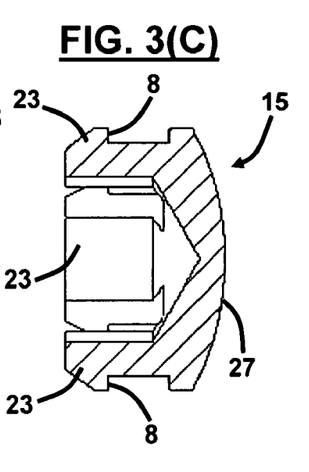
FIG. 3(C) illustrates a cross-sectional side view of the handle top of FIG. 3(A) according to a first embodiment of the invention.

A handle top 15 is depicted in FIGS. 3(A) through 3(C) (with reference to FIGS. 1(A) through 2(D)). The handle top 15 is configured to snap into the top hole 14. The handle top 15 is generally configured as a circular insert having a plurality of snap hooks 23 extending outward from the anterior body surface 25 of the handle top 15. The snap hooks 23 are separated from one another by a groove 26 that generally extends down to the anterior body surface 25. Although any configuration may be used, the posterior body surface 27 is generally configured in a curvilinear fashion to mate with the generally curvilinear shape of the tip portion 2 of the bulbous end 16 of the handle 7. The snap hooks 23 each include a catch 8 configured to engage the lip 6 configured in the top hole 14 of the handle 7. Once the handle top 15 is inserted into the top hole 14 and the catch 8 of the handle top 15 engages the lip 6 of the handle 7, then the handle top 15 is secured to the handle 7.

Figure 4:
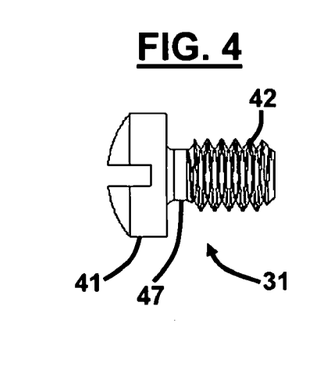
FIG. 4 illustrates a front view of the leafspring screw of FIG. 1(B) according to a first embodiment of the invention.
Figure 5:
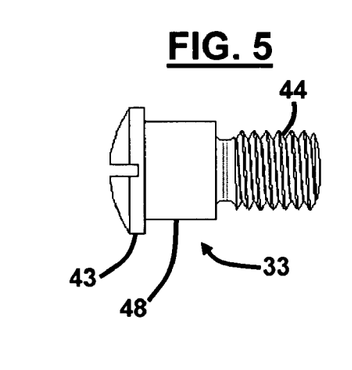
FIG. 5 illustrates a front view of the main pivot screw of FIGS. 1(B) and 12(C) according to an embodiment of the invention.
Figure 6:
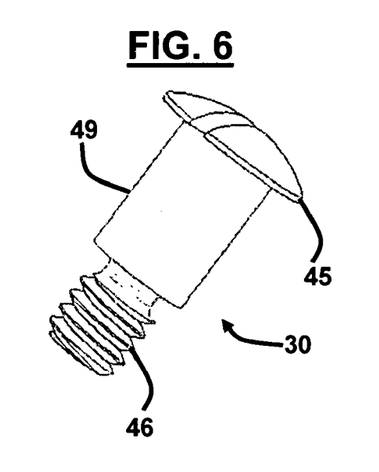
FIG. 6 illustrates a perspective view of the retaining screw of FIG. 1(B) according to a first embodiment of the invention.

FIGS. 4 through 6 illustrate various fixation components 31, 33, 30, respectively, used in conjunction with the first embodiment of the invention and is also shown in FIGS. 1(A) and 1(B). Generally, the fixation components 31, 33, 30 may be configured as screws, although other fixation means may be used such as pins, fasteners, bolts, rivets, nails, etc. The fixation components 31, 33, 30 shown in FIGS. 4 through 6 are embodied as screws, wherein each fixation component 31, 33, 30 includes a head portion 41, 43, 45, respectively, a neck portion 47, 48, 49, respectively, and a body portion 42, 44, 46, respectively, extending from the neck portion 47, 48, 49, respectively, wherein the body portion 42, 44, 46 may be threaded.

Figure 7A:
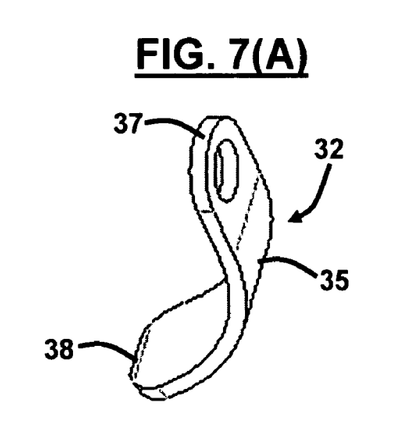
FIG. 7(A) illustrates a perspective view of the leafspring of FIG. 1(B) according to a first embodiment of the invention.
Figure 7B:
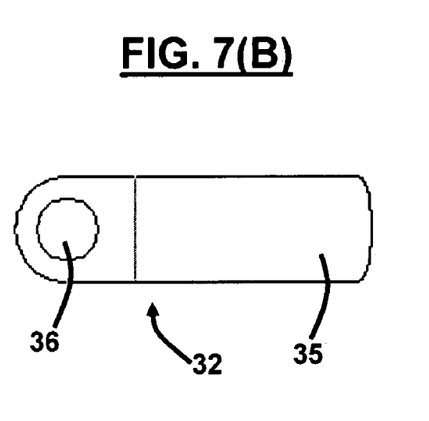
FIG. 7(B) illustrates a top view of the leafspring of FIG. 7(A) according to a first embodiment of the invention.
Figure 7C:
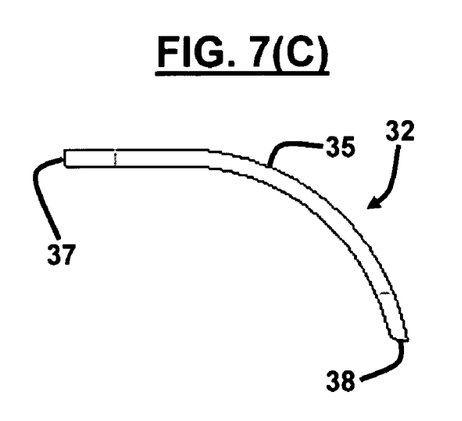
FIG. 7(C) illustrates a side view of the leafspring of FIG. 7(A) according to a first embodiment of the invention.
Figure 8:
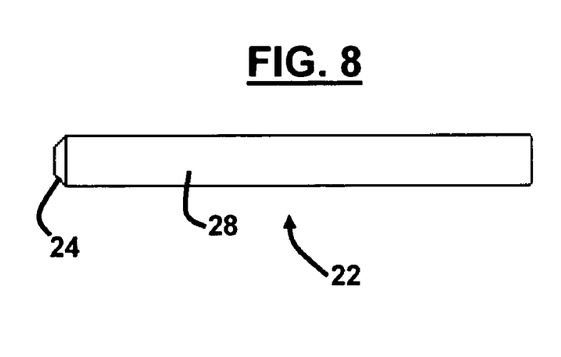
FIG. 8 illustrates a side view of the cross pin of FIG. 1(B) according to a first embodiment of the invention.

FIGS. 7(A) through 7(C) illustrate a leafspring 32 used in conjunction with the first embodiment of the invention and is also shown in FIG. 1(B). The leafspring 32 includes a generally curved body 35 having a first and second end 37, 38, respectively with a hole 36 configured in one of the ends (for example first end 37). Additionally, the cross pin 22 of FIG. 1(B) is further shown in FIG. 8, wherein the cross pin 22 includes a generally elongated body 28 preferably having a tapered end 24. The cross pin 22 is configured to fit into hole 20 of the handle 7 shown in FIGS. 2(B) and 2(D).

Figure 9:
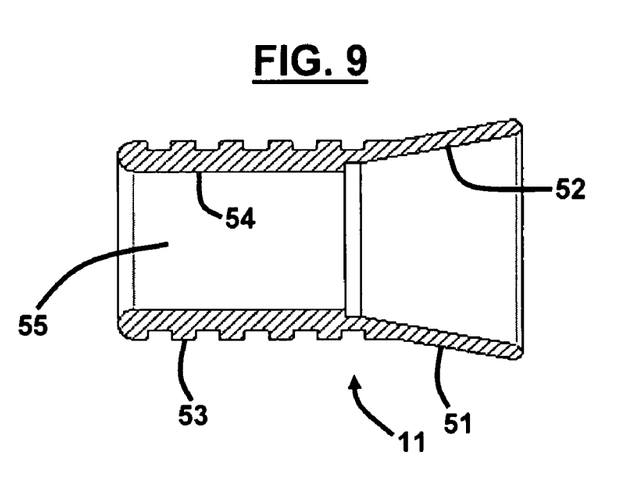
FIG. 9 illustrates a cross-sectional view of the sleeve of FIG. 1(A) according to a first embodiment of the invention.
Figure 10A:
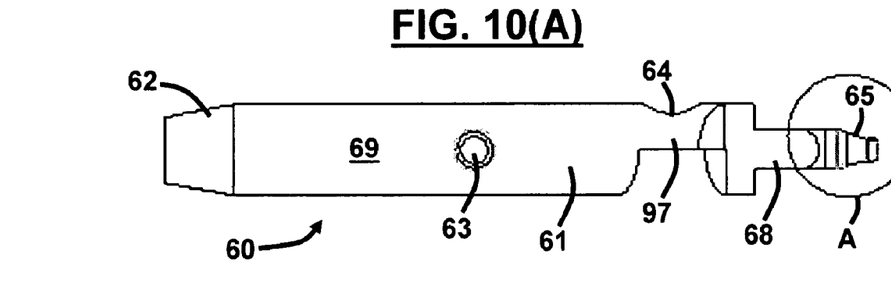
FIG. 10(A) illustrates a top view of the first arm of the screwdriver of FIG. 1(A) according to a first embodiment of the invention.
Figure 10B:
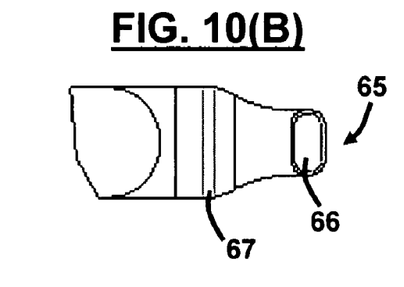
FIG. 10(B) illustrates an isolated magnified view of the encircled area "A" of FIG. 10(A) according to a first embodiment of the invention.
Figure 10C:
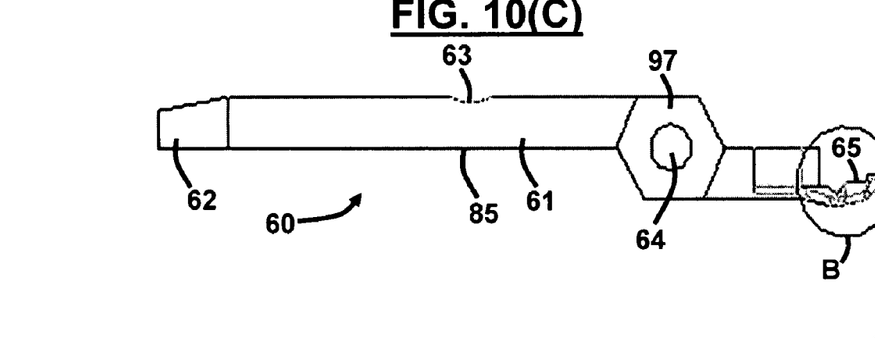
FIG. 10(C) illustrates a side view of the first arm of the screwdriver of FIG. 1(A) according to a first embodiment of the invention.
Figure 10D:
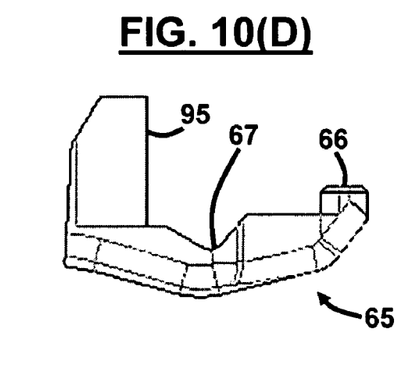
FIG. 10(D) illustrates an isolated magnified view of the encircled area "B" of FIG. 10(C) according to a first embodiment of the invention.
Figure 10E:
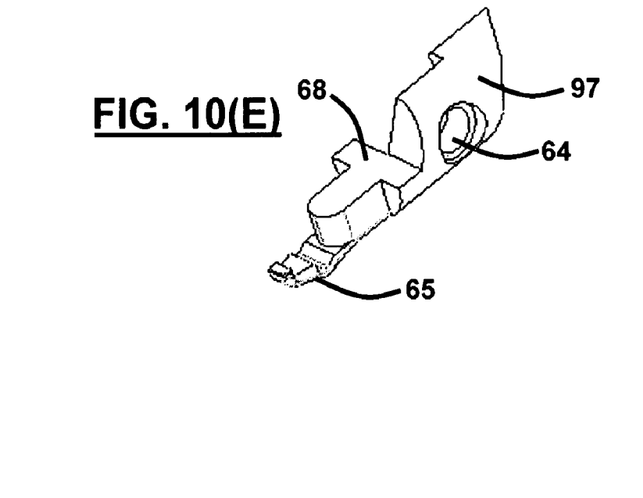
FIG. 10(E) illustrates an isolated perspective view of the prong end of the first arm of FIGS. 10(A) through 10(D) according to a first embodiment of the invention.
Figure 11A:
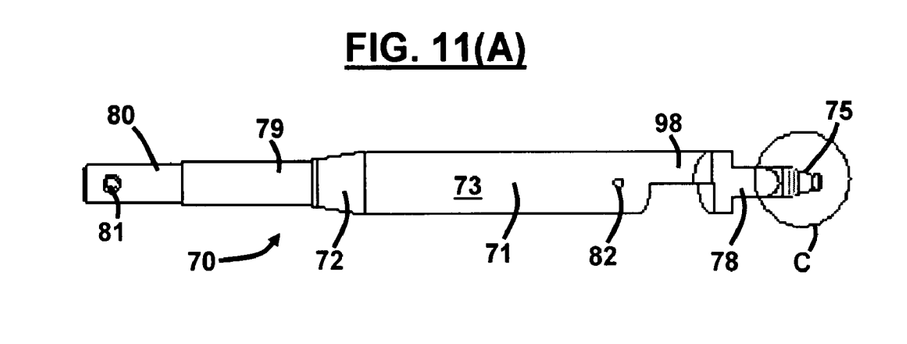
FIG. 11(A) illustrates a top view of the second arm of the screwdriver of FIG. 1(A) according to a first embodiment of the invention.
Figure 11B:
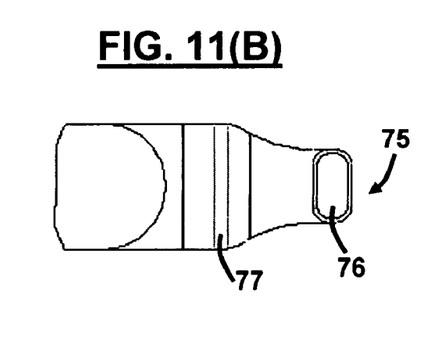
FIG. 11(B) illustrates an isolated magnified view of the encircled area "C" of FIG. 11(A) according to a first embodiment of the invention.
Figure 11C:
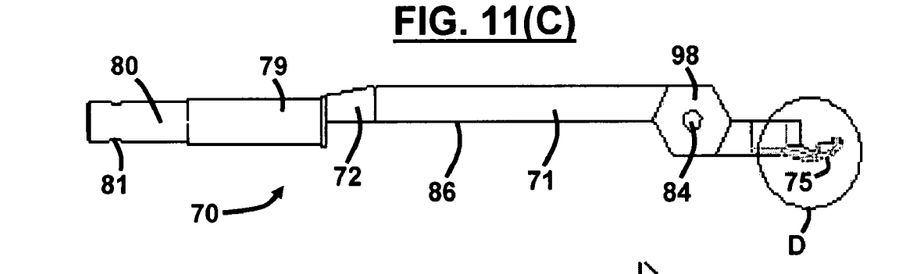
FIG. 11(C) illustrates a side view of the second arm of the screwdriver of FIG. 1(A) according to a first embodiment of the invention.
Figure 11D:
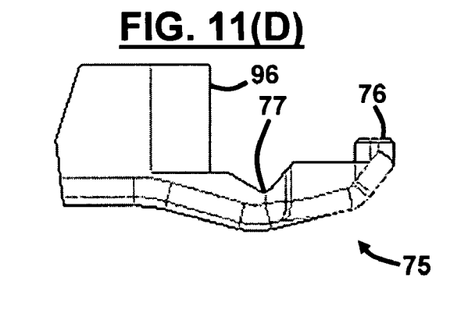
FIG. 11(D) illustrates an isolated magnified view of the encircled area "D" of FIG. 11(C) according to a first embodiment of the invention.
Figure 11E:
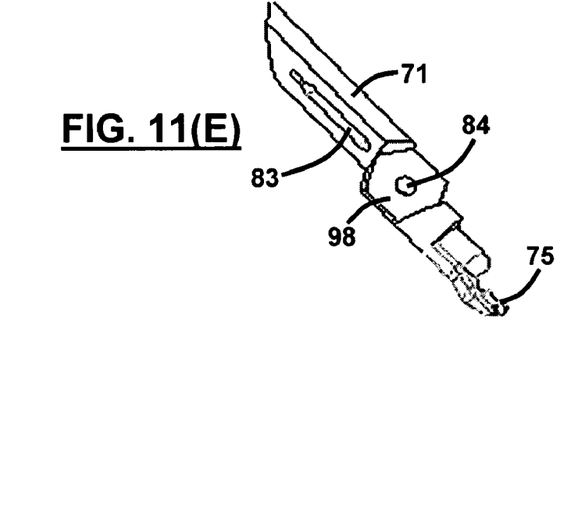
FIG. 11(E) illustrates an isolated perspective view of the prong end of the second arm of FIGS. 11(A) through 11(D) according to a first embodiment of the invention.

The sleeve 11 of FIGS. 1(A) and 1(B) is further cross-sectionally illustrated in FIG. 9. The sleeve 11 includes a generally tapered end 51 having an inner tapered wall 52. Additionally, the sleeve 11 includes a generally elongated cylindrical gripping end 53 adjacent to the tapered end 51, wherein the gripping end 53 has a generally round inner wall 54. The sleeve 11 includes a hollow middle 55, which extends the entire length of the sleeve 11 (i.e., from the gripping end 53 to the tapered end 51).

The attachment mechanism 9 of FIGS. 1(A) and 1(B) generally includes two arms 60, 70. The first arm 60 is further illustrated in FIGS. 10(A) through 10(E) (with reference to FIGS. 1(A) through 9). The first arm 60 generally comprises a shaft portion 61 having a tapered end 62 and a prong end 65 opposite to the tapered end 62. Preferably, a hexagonally-shaped linking portion 97 joins the shaft portion 61 to the prong end 65. The shaft portion 61 includes a preferably centrally located hole 63. Moreover, the shaft portion 61 further includes a generally curved outer wall surface 69 and a generally flat inner wall surface 85. The linking portion 97 also includes a hole 64 configured through the entire thickness of the linking portion 97. Preferably, the hole 64 has threads (not shown) circumferentially configured around the outer periphery of the hole 64. Furthermore, a generally flat alignment portion 68 is configured between the prong end 65 and the linking portion 97. The prong end 65 further includes a prong tip 66 configured at the free end of the prong end 65, an indent portion 67 configured between the prong tip 66 and the alignment portion 68, and a driving wall 95 configured at the edge of the alignment portion 68.

The second arm 70 of the attachment mechanism 9 of FIGS. 1(A) and 1(B) is further depicted in FIGS. 11(A) through 11(E) (with reference to FIGS. 1(A) through 10(E)). The second arm 70 generally comprises a shaft portion 71 having a prong end 75 similarly configured to the prong end 65 of the first arm 60. Preferably, a hexagonally-shaped linking portion 98 joins the shaft portion 71 to the prong end 75. The shaft portion 71 includes an offset hole 82. Moreover, the shaft portion 71 further includes a generally curved outer wall surface 73 and a generally flat inner wall surface 86. The linking portion 98 also includes an elongated groove 83. Additionally, a hole 84 is configured through the entire thickness of the linking portion 98 and dimensioned similarly to the hole 64 of the linking portion 97 of the first arm 60. Preferably, the hole 84 has threads (not shown) circumferentially configured around the outer periphery of the hole 84. Furthermore, a generally flat alignment portion 78 is configured between the prong end 75 and the linking portion 98. The prong end 75 further includes a prong tip 76 configured at the free end of the prong end 75, an indent portion 77 configured between the prong tip 76 and the alignment portion 78, and a driving wall 96 configured at the edge of the alignment portion 78.

The shaft portion 71 is adjacent to a tapered section 72, which has a thickness similar to the thickness of the shaft portion 71. Adjacent to the tapered section 72 is a fully cylindrical first handle attachment shaft 79, which connects to a second handle attachment shaft 80, which has a hole 81 disposed through an entire thickness therein. Preferably, the second handle attachment shaft 80 is dimensioned slightly smaller than the first handle attachment shaft 81 and is also in a cylindrical configuration.

With reference to FIGS. 1(A) through 11(E), the first embodiment of the screwdriver 5 operates in the following manner. The leafspring 32 is attached to the second arm 70 by placing the fixation component 31 through the hole 36 of the leafspring 32 and securing it within hole 82 of the groove 83 of the second arm 70. The second end 38 of the leafspring 32 is free to engage the first arm 60 and provides a bending resistance against the first arm 60. The first and second arms 60, 70, respectively are aligned and connected via fixation component 33, which is secured within holes 64, 84 of the first and second arms 60, 70, respectively. Furthermore, fixation component 30 is secured within hole 63 of the first arm 60 and extends through to a correspondingly aligned hole (not shown) in the second arm 70. The neck portion 49 of the fixation component 30 is generally cylindrical, smooth, and elongated to allow the fixation component 30 to freely move within hole 63. However, the head portion 45 of the fixation component 30 does not extend beyond the surface 69 of the shaft portion 61 of the first arm 60. Moreover, the body portion 46 of the fixation component 30 is anchored into the second arm 70 thereby preventing the fixation component 30 from becoming dislodged. The fixation component 30 acts as a stop to limit the distance of separation between the first arm 60 and the second arm 70.

As shown in FIG. 1(B), the first and second arms 60, 70 are naturally in an open configuration due to the resistance provided by the leafspring 32 pushing the first arm 60 away from the second arm 70, thereby moving the prong ends 65, 75 away from one another. The fixation component 33 provides a pivot point for the first and second arms 60, 70 to move in a scissor-like manner. When, the first arm 60 is squeezed closer to the second arm 70, then the leafspring 32 pushes against the first arm 60 thereby creating resistance against the first arm 60, which keeps the arms 60, 70 in an open configuration.

The first and second handle attachment shafts 79, 80 of the second arm 70 are next inserted through the hollow middle 55 of the sleeve 11, first through the tapered end 51 and onto and extending out past the gripping end 53. The diameter of the hollow middle 55 of the sleeve 11 is configured to be slightly larger than the diameter of the first and second handle attachment shafts 79, 80 of the second arm 70, thereby allowing the sleeve 11 to slide on the second arm 70. Next, the second handle attachment shaft 80 is inserted into the attachment bore 21 of the handle 7. Thereafter, the cross pin 22 is inserted into the hole 20 of the handle 7, preferably with the tapered end 24 of the cross pin 22 facing the outer surface of the handle 7, thereby mating with the general configuration of the outer shape of the handle 7. However, the cross pin 22 can also be inserted the other way; with the tapered end 24 inside the handle 7. During insertion, the cross pin 22 is inserted into hole 81 of the second handle attachment shaft 80, thereby locking handle 7 to the second arm 70, and thus, locking the entire attachment mechanism 9.

When the first arm 60 is squeezed against the second arm 70, it is considered to be in a closed configuration. Moreover, in the closed configuration, the flat inner wall surface 85 of the first arm 60 mates with the flat inner wall surface 86 of the second arm 70, which simultaneously mates the tapered end 62 of the first arm 60 with the tapered section 72 of the second arm 70. The tapered end 51 of the sleeve 11 is configured to be able to slide over the mated tapered end 62 and tapered section 72 of the attachment mechanism 9. The attachment mechanism 9 can be locked in the closed configuration by moving the sleeve 11 over the mated tapered end 62 and tapered section 72 of the attachment mechanism 9, and pushing the sleeve 11 until it will no longer slide, which occurs when the mated tapered end 62 and tapered section 72 of the attachment mechanism 9 reaches the generally round inner wall 54 of the gripping end 53 of the sleeve 11. As such, once, the second arm 70 is secured into the handle 7, the sleeve 11 is prevented from moving past the bottom end 13 of the handle 7 on one side and, once the first and second arms 60, 70 are pushed together, the sleeve 11 is prevented from moving past the mated tapered end 62 and tapered section 72 of the attachment mechanism 9. In order to once again place the attachment mechanism 9 into an open configuration, the sleeve 11 is moved towards the handle 7, thereby causing the leafspring 32 to push the first arm 60 away from the second arm 70, which causes the prong ends 65, 75 to move further away from one another. In the open configuration, the sleeve 11 generally rests on the first handle attachment shaft 79 of the second arm 70.

FIGS. 12(A) through 12(D) illustrate an attachment mechanism 109 according to a second embodiment of the invention. Generally, the attachment mechanism 109 generally comprises a first arm 160, a second arm 170, and a locking sleeve 111. According to the second embodiment, the attachment mechanism 109 is adapted to attach to the handle 7 of FIGS. 2(A) through 2(D) in a manner similar to the first embodiment, but can be removed if necessary.

Figure 12A:
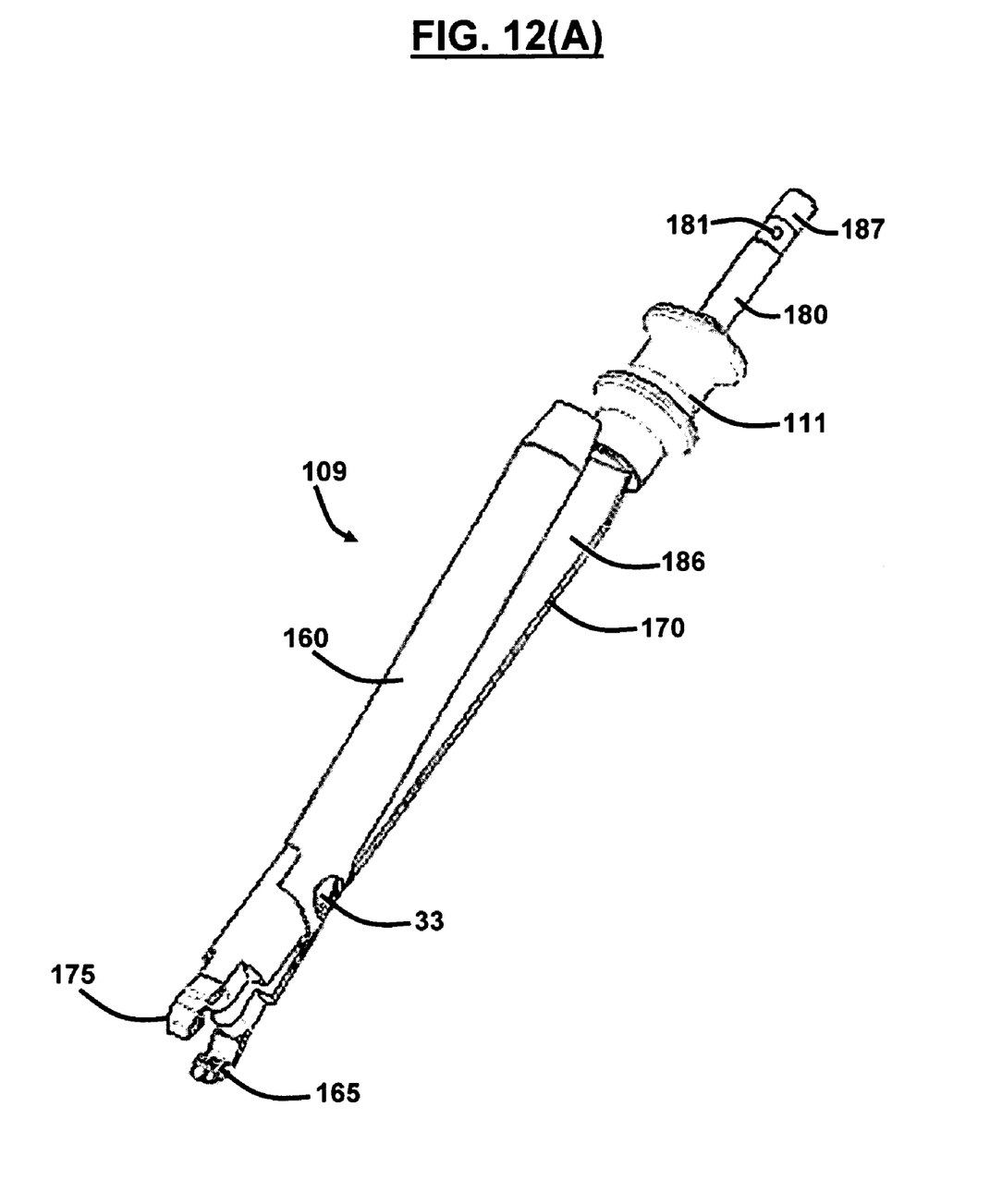
FIG. 12(A) illustrates a perspective view of a screwdriver attachment mechanism according to a second embodiment of the invention.
Figure 12B:
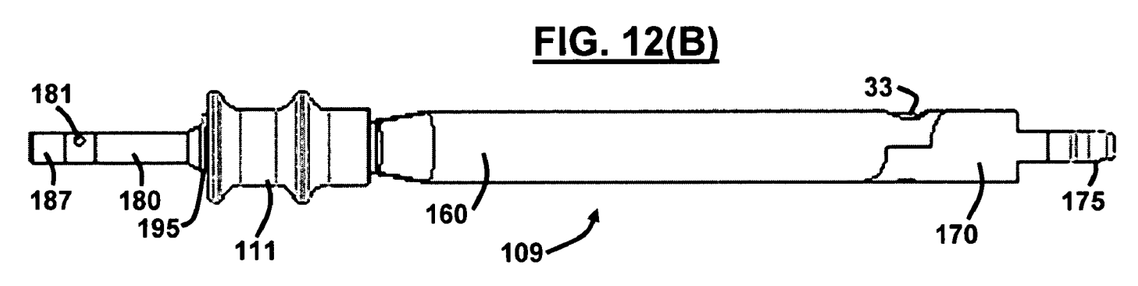
FIG. 12(B) illustrates a top view of the screwdriver attachment mechanism of FIG. 12(A) according to a second embodiment of the invention.
Figure 12C:
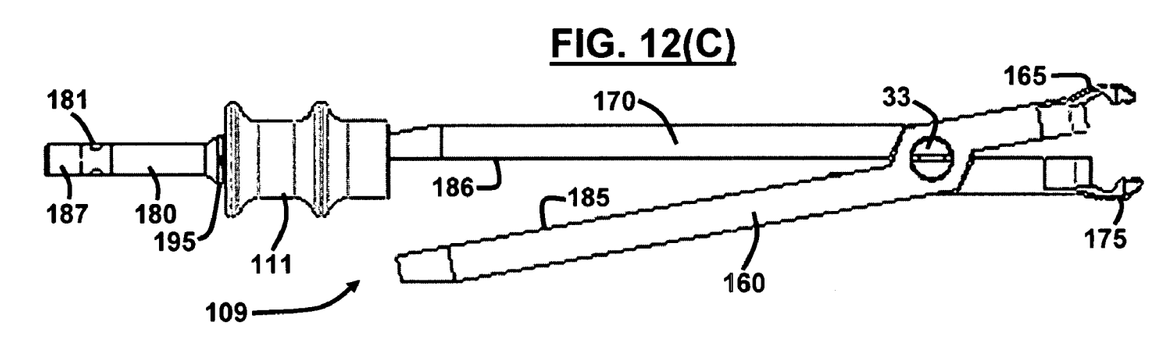
FIG. 12(C) illustrates a side view of the screwdriver attachment mechanism of FIG. 12(A) according to a second embodiment of the invention.
Figure 12D:
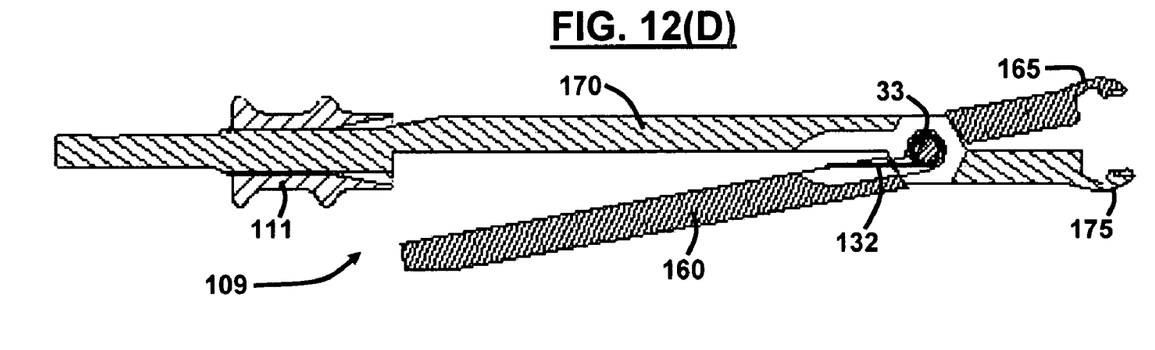
FIG. 12(D) illustrates a cross-sectional side view of the screwdriver attachment mechanism of FIG. 12(A) according to a second embodiment of the invention.
Figure 13A:
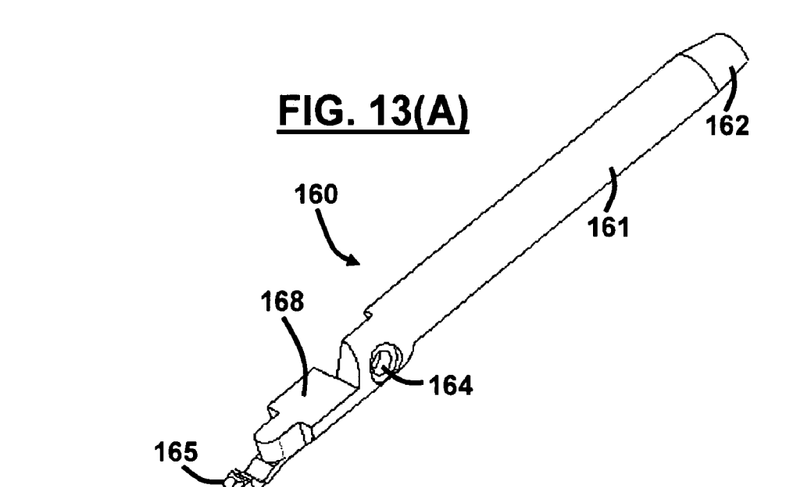
FIG. 13(A) illustrates a perspective view of a first arm of the screwdriver attachment mechanism of FIG. 12(A) according to a second embodiment of the invention.
Figure 13B:
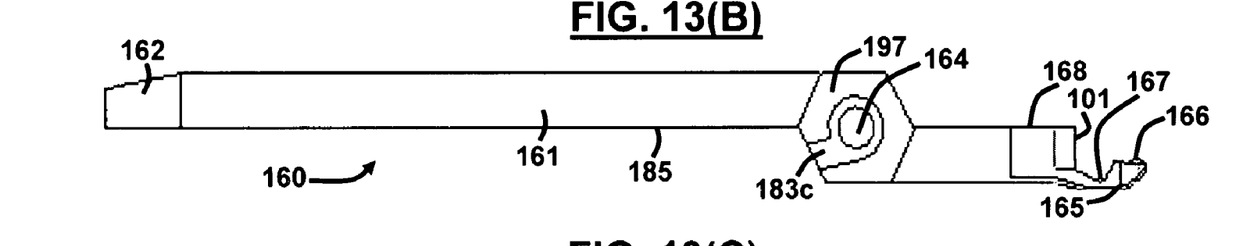
FIG. 13(B) illustrates a side view of the first arm of the screwdriver attachment mechanism of FIG. 13(A) according to a second embodiment of the invention.
Figure 13C:
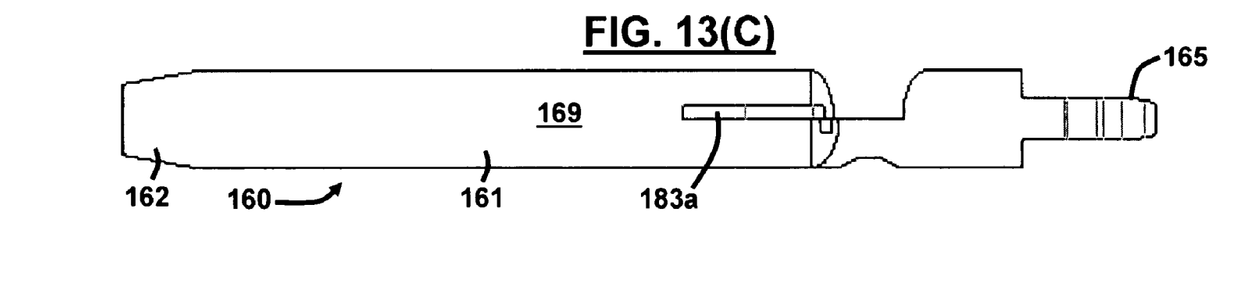
FIG. 13(C) illustrates a top view of the first arm of the screwdriver attachment mechanism of FIG. 13(A) according to a second embodiment of the invention.

The first arm 160 of the attachment mechanism 109 of FIGS. 12(A) through 12(D) is further depicted in FIGS. 13(A) through 13(C) (with reference to FIGS. 12(A) through 12(D)). The first arm 160 generally comprises a shaft portion 161 having a tapered end 162 and a prong end 165 opposite to the tapered end 162. Preferably, a hexagonally-shaped linking portion 197 joins the shaft portion 161 to the prong end 165. A lateral slot 183*a* and a circular slot 183*c*, which connect to one another, are configured in the linking portion 197 and in the shaft portion 161 located near the linking portion 197. Moreover, the shaft portion 161 further includes a generally curved outer wall surface 169 and a generally flat inner wall surface 185. The linking portion 197 also includes a hole 164 configured through the entire thickness of the linking portion 197. Preferably, the hole 164 has threads (not shown) circumferentially configured around the outer periphery of the hole 164. Furthermore, a generally flat alignment portion 168 is configured between the prong end 165 and the linking portion 197. The prong end 165 further includes a prong tip 166 configured at the free end of the prong end 165, an indent portion 167 configured between the prong tip 166 and the alignment portion 168, and a driving wall 101 configured at the edge of the alignment portion 168.

Figure 14A:
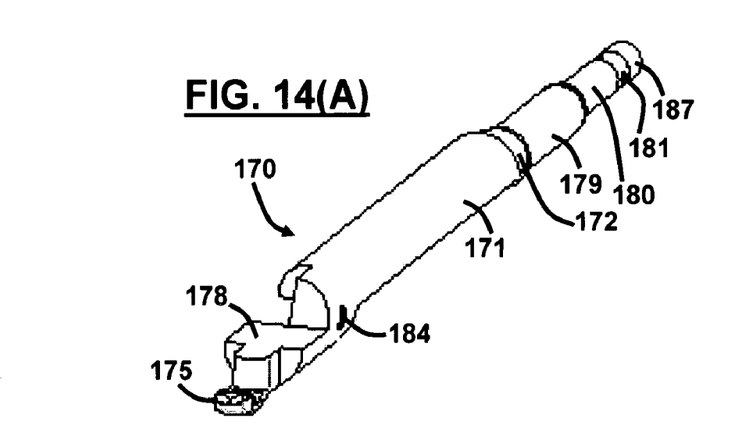
FIG. 14(A) illustrates a perspective view of a second arm of the screwdriver attachment mechanism of FIG. 12(A) according to a second embodiment of the invention.
Figure 14B:
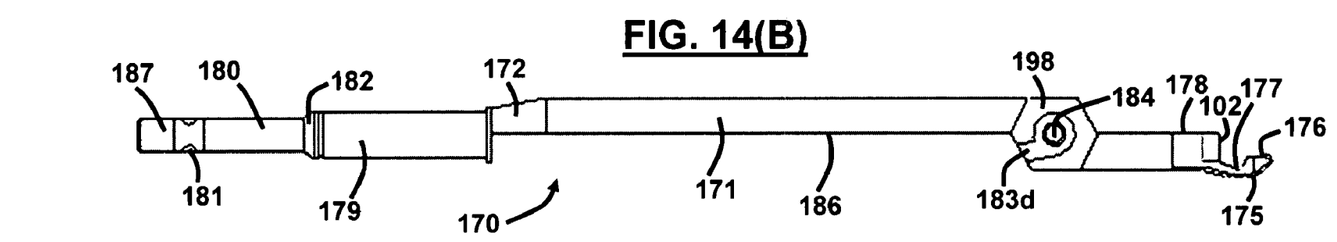
FIG. 14(B) illustrates a side view of the second arm of the screwdriver attachment mechanism of FIG. 14(A) according to a second embodiment of the invention.
Figure 14C:
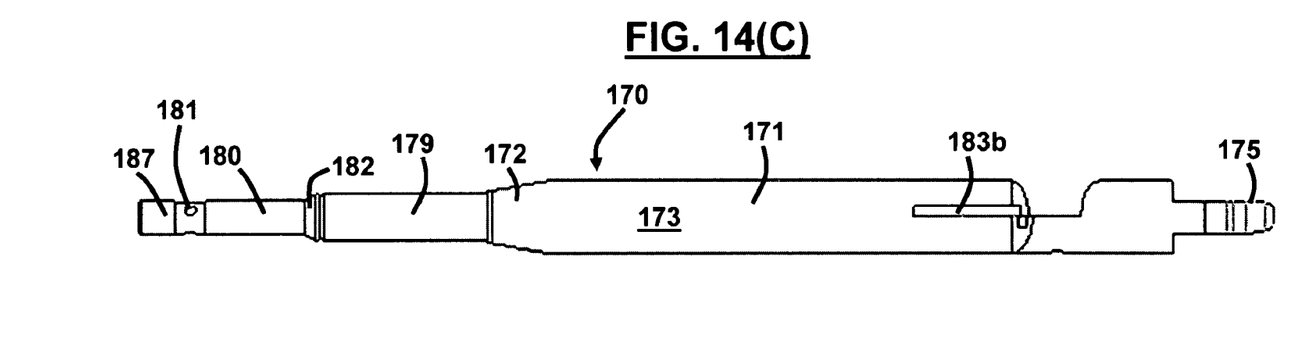
FIG. 14(C) illustrates a top view of the second arm of the screwdriver attachment mechanism of FIG. 14(A) according to a second embodiment of the invention.

The second arm 170 of the attachment mechanism 109 of FIGS. 12(A) through 12(D) is further depicted in FIGS. 14(A) through 14(C) (with reference to FIGS. 12(A) through 13(C)). The second arm 170 generally comprises a shaft portion 171 having a prong end 175 similarly configured to the prong end 75 of the second arm 70 of the first embodiment (as shown in FIGS. 11(A) through 11(E)). Preferably, a hexagonally-shaped linking portion 198 joins the shaft portion 171 to the prong end 175. A lateral slot 183*b* and a circular slot 183*d*, which connect to one another, are configured in the linking portion 198 and in the shaft portion 171 located near the linking portion 198. Moreover, the shaft portion 171 further includes a generally curved outer wall surface 173 and a generally flat inner wall surface 186. Additionally, a hole 184 is configured through the entire thickness of the linking portion 198 and dimensioned similarly to the hole 164 of the linking portion 197 of the first arm 160. Preferably, the hole 184 has threads (not shown) circumferentially configured around the outer periphery of the hole 184. Furthermore, a generally flat alignment portion 178 is configured between the prong end 175 and the linking portion 198. The prong end 175 further includes a prong tip 176 configured at the free end of the prong end 175, an indent portion 177 configured between the prong tip 176 and the alignment portion 178, and a driving wall 102 configured at the edge of the alignment portion 168.

The shaft portion 171 is adjacent to a tapered section 172, which has a thickness similar to the thickness of the shaft portion 171. Adjacent to the tapered section 172 is a fully cylindrical first handle attachment shaft 179, which connects to a smaller tapered section 182, which then connects to a second handle attachment shaft 180, which has a hole 181 disposed through an entire thickness therein. Preferably, the second handle attachment shaft 180 is dimensioned slightly smaller than the first handle attachment shaft 181 and is also in a cylindrical configuration. A tip 187, which is diametrically dimensioned similarly to the second handle attachment shaft 180, is configured next to the second handle attachment shaft 180 and is positioned at an opposite end to the prong end 175 of the second arm 170.

Figure 15A:
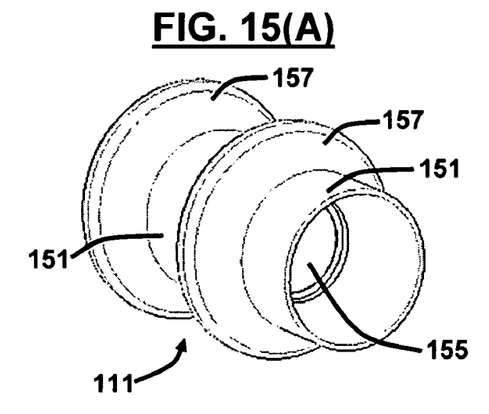
FIG. 15(A) illustrates a perspective view of the sleeve of FIG. 12(A) according to a second embodiment of the invention.
Figure 15B:
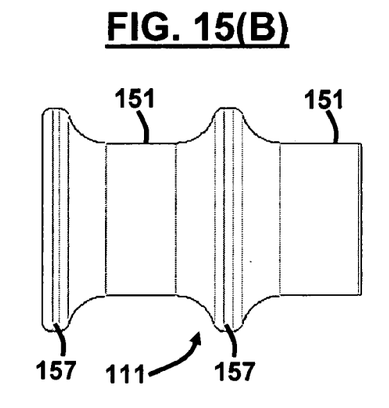
FIG. 15(B) illustrates a side view of the sleeve of FIG. 15(A) according to a second embodiment of the invention.
Figure 15C:
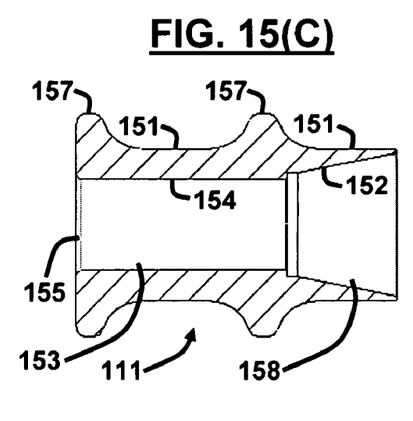
FIG. 15(C) illustrates a cross-sectional side view of the sleeve of FIG. 15(A) according to a second embodiment of the invention.
Figure 16:
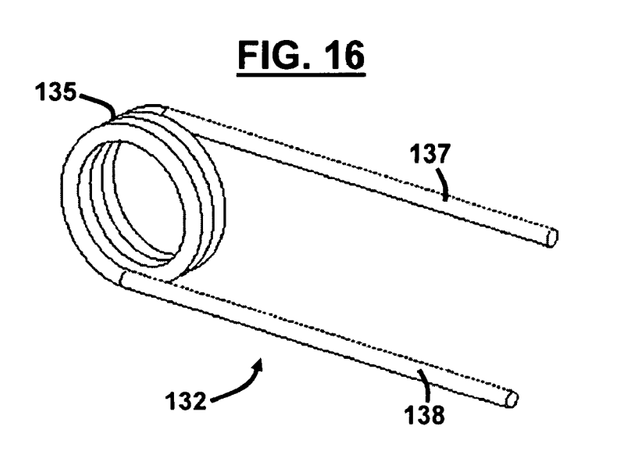
FIG. 16 illustrates a perspective view of the torsion spring of FIG. 12(D) according to a second embodiment of the invention.
Figure 17:
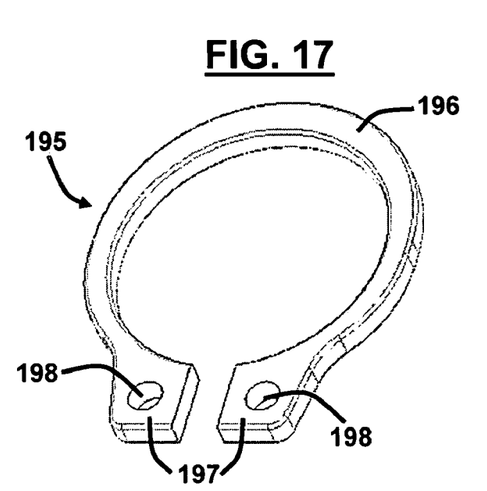
FIG. 17 illustrates a perspective view of the retaining clip of FIGS. 12(B) and 12(C) according to a second embodiment of the invention.

The locking sleeve 111 of FIGS. 12(A) through 12(D) is further shown in FIGS. 15(A) through 15(C). Generally, the locking sleeve 111 comprises a tubular structure 151 having a plurality of spaced apart circular flanges 157 configured around the tubular structure 151. The tubular structure 151 has a hollow inner portion 155 and has a cylindrical portion 153 having a generally cylindrical inner surface 154. Additionally, the tubular structure 151 has a tapered end 158 having a generally tapered inner surface 152. The torsion spring 132 of FIG. 12(D) is shown with more particularity in FIG. 16. The torsion spring 132 comprises a coiled central portion 135 and a pair of elongated ends 137, 138 distally located from the coiled central portion 135. The retaining clip 195 of FIGS. 12(B) and 12(C) is further shown in FIG. 17. The retaining clip 195 may be formed in any appropriate configuration. For example, the retaining clip 195 may be formed in a generally circular ring-like configuration comprising a ring-like body portion 196 terminating in a pair of end portions 197, wherein the end portions 197 each comprise a hole 198. As shown in the example in FIG. 17, the end portions 197 are separate from one another.

With reference to FIGS. 2(A) through 2(D), FIG. 5, and FIGS. 12(A) through 17, the second embodiment of the invention operates in the following manner. The torsion spring 132 is attached to the second arm 170 by inserting one of the elongated ends 137 in the lateral slot 183b of the second arm 170, and placing one side of the coiled central portion 135 in the circular slot 183d. Then, the first arm 160 is connected to the second arm 170 by, first, placing the other elongated end 138 of the torsion spring 132 in the lateral slot 183a of the first arm 160, and placing the exposed half of coiled central portion 135 of the torsion spring 132 in the circular slot 183c of the first arm. The first and second arms 160, 170, respectively are aligned and connected via fixation component 33, which is secured within holes 164, 184 of the first and second arms 160, 170, respectively. By placing the torsion spring 132 in such a configuration as described above, the torsion spring 132 provides a bending resistance against the first arm 160 once the attachment mechanism 109 is secured in the handle 7.

As shown in FIGS. 12(C) and 12(D), the first and second arms 160, 170 are naturally in an open configuration due to the resistance provided by the torsion spring 132 pushing the first arm 160 away from the second arm 170, thereby moving the prong ends 165, 175 away from one another. The fixation component 133 provides a pivot point for the first and second arms 160, 170 to move in a scissor-like manner. When, the first arm 160 is squeezed closer to the second arm 170, then the torsion spring 132 pushes against the first arm 160 thereby creating resistance against the first arm 160, which keeps the arms 160, 170 in an open configuration.

The first and second handle attachment shafts 179, 180 and tip 187 of the second arm 170 are next inserted through the hollow inner portion 155 of the locking sleeve 111, first through the tapered end 151 and onto and extending out past the cylindrical portion 153. The diameter of the hollow inner portion 155 of the locking sleeve 111 is configured to be slightly larger than the diameter of the first and second handle attachment shafts 179, 180 of the second arm 170, thereby allowing the locking sleeve 111 to slide on the second arm 170. Thereafter the retaining clip 195 is secured to the locking sleeve 111 in such a manner as to prevent the locking sleeve 111 from moving laterally past the retaining clip 195. Preferably, the retaining clip 195 is positioned between the tapered section 182 and the first handle attachment shaft 179 of the second arm 170. Securing components (not shown) such as screws may be used to further secure the retaining clip 195 to the second arm 170 by fixing the screws in the holes 198 of the retaining clip 195.

Next, the tip 187 and second handle attachment shaft 180 are inserted into the attachment bore 21 of the handle 7. Thereafter, the cross pin 22 is inserted into the hole 20 of the handle 7, preferably with the tapered end 24 of the cross pin 22 facing the outer surface of the handle 7, thereby mating with the general configuration of the outer shape of the handle 7. However, the cross pin 22 can also be inserted the other way; with the tapered end 24 inside the handle 7. During insertion, the cross pin 22 is inserted into hole 181 of the second handle attachment shaft 180, thereby locking handle 7 to the second arm 170, and thus, locking the entire attachment mechanism 109.

When the first arm 160 is squeezed against the second arm 170, it is considered to be in a closed configuration. Moreover, in the closed configuration, the flat inner wall surface 185 of the first arm 160 mates with the flat inner wall surface 186 of the second arm 170, which simultaneously mates the tapered end 162 of the first arm 160 with the tapered section 172 of the second arm 170. The tapered end 151 of the locking sleeve 111 is configured to be able to slide over the mated tapered end 162 and tapered section 172 of the attachment mechanism 109. The attachment mechanism 109 can be locked in the closed configuration by moving the locking sleeve 111 over the mated tapered end 162 and tapered section 172 of the attachment mechanism 109, and pushing the sleeve 111 until it will no longer slide, which occurs when the mated tapered end 162 and tapered section 172 of the attachment mechanism 109 reaches the generally cylindrical inner surface 154 of the cylindrical portion 153 of the locking sleeve 111.

Once the first and second arms 160, 170 are pushed together, the locking sleeve 111 is prevented from moving past the mated tapered end 162 and tapered section 172 of the attachment mechanism 109. In order to once again place the attachment mechanism 109 into an open configuration, the locking sleeve 111 is moved towards the handle 7, thereby causing the torsion spring 132 to push the first arm 160 away from the second arm 170, which causes the prong ends 165, 175 to move further away from one another. In the open configuration, the locking sleeve 111 generally rests on the first handle attachment shaft 179 of the second arm 170.

The embodiments of the invention allow it to be used in any number of different applications. An example of one such application is inserting a pedicle screw assembly, such as that described in U.S. patent application Ser. No. 11/045,908, filed Jan. 28, 2005 and entitled, "Polyaxial Pedicle Screw Assembly," (hereinafter referred to as the "'908 application") the complete disclosure of which in its entirety is herein incorporated by reference. Taking the first embodiment of the invention as an example together with the teachings of the '908 application, generally, a pre-attached bone screw and screw head assembly of the '908 application is engaged by the screwdriver 5 when the attachment mechanism 9 is in the open configuration. Here, the screw head of the '908 application may be inserted in the open pocket 4 (shown in FIG. 1(B)) of the prong ends 65, 75 of the attachment mechanism 9, wherein the screw head may rest against the driving wall 95, 96 of the prong ends 65, 75, respectively. Then, once the attachment mechanism 9 is articulated into the closed configuration, the prong tips 66, 76 of the prong ends 65, 75, respectively engage groove features of the bone screw of the '908 application.

While the embodiments of the invention are best utilized in a surgical pedicle screw assembly application, as described above, those skilled in the art would readily understand that the embodiments of the invention may be practiced in any application, and particularly, where the component to be driven (i.e., screwed or fastened) has an unconventional shape and preferably has a gripping feature to receive the prong tips 66, 76/166, 176 of the embodiments of the invention. Although, so long as the grip of the prong ends 65, 75/165, 175 is sufficiently strong, no specific gripping feature is necessary on the driven component. Furthermore, the embodiments of the invention may be manufactured in any customized size depending on the particular application.

Generally, the embodiments of the invention provide a screwdriver 5 having an attachment mechanism 9, 109 which includes a bias element 32, 132, respectively for triggering scissor-like actuation of a pair of prongs 65, 75/165, 175, respectively, wherein, in one application example, the prongs 65, 75/165, 175 may engage a combined screw head and bone screw of a pedicle screw assembly.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments of the invention have been described in terms of preferred embodiments, those skilled in the art will recognize that the embodiments of the invention can be practiced with modification within the spirit and scope of the appended claims.

What is claimed is:

1. A screwdriver attachment comprising:
    a plurality of arms pivotally attached to one another, wherein each arm comprises a substantially semi-circular bifurcated wall having a substantially flat surface with a prong outwardly extending from a middle portion of said wall, wherein each said prong comprises a gripping portion extending from a block portion comprising a tapered end connecting to planar side surfaces, wherein when said plurality of arms are squeezed together, the arms form a substantially cylindrical shape such that an outer lateral edge of each said prong extends beyond a width defined by a diameter of said cylindrical shape, and wherein a width of an entirety of said block portion is approximately half of said width defined by said diameter of said cylindrical shape;
    a bias element mounted in at least one of said plurality of arms; and
    a sleeve slidably mounted around at least one of said plurality of arms.

2. The screwdriver attachment of claim 1, all the limitations of which are incorporated herein by reference, wherein said plurality of arms comprise a first arm and a second arm.

3. The screwdriver attachment of claim 1, all the limitations of which are incorporated herein by reference, wherein each of said plurality of arms comprise a prong end that securely fits onto a pedicle bone screw assembly.

4. The screwdriver attachment of claim 2, all the limitations of which are incorporated herein by reference, further comprising a stop component adapted to limit a distance of separation between said first arm and said second arm.

5. The screwdriver attachment of claim 1, all the limitations of which are incorporated herein by reference, wherein said bias element comprises a spring.

6. The screwdriver attachment of claim 1, all the limitations of which are incorporated herein by reference, wherein each of said plurality of arms comprise a tapered section.

7. The screwdriver attachment of claim 6, all the limitations of which are incorporated herein by reference, wherein said sleeve comprises an inner tapered wall adapted to engage said tapered section of each of said plurality of arms.

8. A scissor-action tool comprising:
    a first arm;
    a second arm pivotally attached to said first arm;
    a bias element adjacent to the first and second arms; and
    a sleeve mounted over said second arm,
    wherein each arm comprises a prong end comprising a bifurcated back wall having a prong outwardly extending from a middle portion of said back wall, wherein each said prong comprises:
        a block portion comprising a tapered end; and
        a gripping portion extending from said tapered end, wherein said gripping portion comprises a prong tip positioned orthogonal to said back wall,
    wherein when said first arm and second arm are squeezed together, the arms form a substantially cylindrical shape, and
    wherein a thickness of said block portion is approximately half of a width defined by a diameter of said cylindrical shape.

9. The tool of claim 8, all the limitations of which are incorporated herein by reference, wherein said prong end securely fits onto a pedicle bone screw assembly.

10. The tool of claim 8, all the limitations of which are incorporated herein by reference, further comprising a stop component adapted to limit a distance of separation between said first and second arms.

11. The tool of claim 8, all the limitations of which are incorporated herein by reference, wherein said bias element comprises a spring.

12. The tool of claim 8, all the limitations of which are incorporated herein by reference, wherein each of said first and second arms comprises a tapered section.

13. The tool of claim 12, all the limitations of which are incorporated herein by reference, wherein said sleeve is slidably mountable over said first arm and comprises an inner tapered wall adapted to engage said tapered section of each of said first and second arms.

14. A screwdriver comprising:
a handle;
a first arm;
a second arm connected to said handle and said first arm;
a spring in contact with the first and second arms; and
a sleeve mounted around said second arm,
wherein each arm comprises a prong end comprising a substantially semi-circular bifurcated back wall having a substantially flat surface with a prong outwardly extending from only a middle portion of said back wall, wherein each said prong comprises:
  a block portion comprising:
    a tapered end; and
    substantially flat and planar side surfaces;
  a gripping portion extending from said tapered end at an obtuse angle; and
  a prong tip extending from said gripping portion and positioned orthogonal to said back wall,
wherein when said first arm and second arm are squeezed together, the arms form a substantially cylindrical shape such that an outer lateral edge of each said prong extends beyond a width defined by a diameter of said cylindrical shape whereby a width of each said prong is less than a width of said cylindrical shape, and
wherein when said first arm and second arm are squeezed together, said substantially flat side surfaces of each said block portion of each said prong come together to form a substantially flat and uniform planar surface.

15. The screwdriver of claim 14, all the limitations of which are incorporated herein by reference, further comprising a stop component adapted to limit a distance of separation between said first and second arms.

16. The screwdriver of claim 14, all the limitations of which are incorporated herein by reference, wherein each of said first and second arms comprises a tapered section.

17. The screwdriver of claim 16, all the limitations of which are incorporated herein by reference, wherein said sleeve is slidably mountable around said first arm and comprises an inner tapered wall adapted to engage said tapered section of each of said first and second arms.

18. The screwdriver of claim 14, all the limitations of which are incorporated herein by reference, wherein said prong end securely fits onto a pedicle bone screw assembly.

19. The screwdriver of claim 18, all the limitations of which are incorporated herein by reference, wherein said prong end is adapted to engage both a rod-housing component and a bone screw component of said pedicle bone screw assembly.

20. The screwdriver of claim 14, all the limitations of which are incorporated herein by reference, wherein said first arm is pivotally connected to said second arm.

* * * * *